United States Patent [19]

Ogata et al.

[11] Patent Number: 5,662,604

[45] Date of Patent: Sep. 2, 1997

[54] MONITORING METHOD OF RENAL LESIONS WITHOUT CLINICAL SIGNS

[75] Inventors: Etsuro Ogata; Kiyoshi Kurokawa; Shunya Uchida, all of Tokyo; Akiko Kishida, Kanagawa, all of Japan

[73] Assignee: Asahi Kasei Kogyo Kabushiki Kaisha, Osaka, Japan

[21] Appl. No.: 495,635

[22] PCT Filed: Feb. 12, 1993

[86] PCT No.: PCT/JP93/00178

§ 371 Date: Sep. 19, 1995

§ 102(e) Date: Sep. 19, 1995

[51] Int. Cl.$^6$ ................................................ A61K 38/00
[52] U.S. Cl. ............................................................ 604/28
[58] Field of Search ............................... 604/49, 19, 21, 604/890.1, 891.1, 892.1, 27, 28, 30, 48–53

[56] References Cited

U.S. PATENT DOCUMENTS

| | | | |
|---|---|---|---|
| 4,469,681 | 9/1984 | Brownlee et al. | 424/178 |
| 5,494,905 | 2/1996 | Hesse et al. | 514/167 |

OTHER PUBLICATIONS

T. Kawagishi et al., "Calcium Metabolism in Diabetes Mellitus", *J. Nutr. Sci. Vitaminol*, vol. 37, (Suppl.), 1991, pp. S51–S56.

Y. Furukawa, "Special/Calcium Metabolism Abnormality Pseudohypoparathyroidism", *Hormone and Clinical*, vol. 40, No. 6, 1992, pp. 585–592.

E. Morita et al., "Clinical Significance of Urinary Enzymes in Diabetes Mellitus", *J. UOEH. Occup. Environ. Heal*, vol. 12, No. 2, 1990, pp. 197–205.

*Primary Examiner*—Manuel Mendez
*Attorney, Agent, or Firm*—Young & Thompson

[57] ABSTRACT

A screening method for detecting renal lesions in diabetic patients not yet exhibiting symptoms of nephropathy, comprising administering a predetermined dose of parathyroid hormone, analogue thereof or derivative thereof to the patients with an albumin excretion rate (AER) of microalbumin being below 15 µg/min., measuring urinary excreted N-acetyl-β-D-glucosaminidase (NAG) and urinary creatinine in urinary samples taken 60±10 minutes before and after administration of PTH, and monitoring the increased ratio of urinary excreted NAG (U/g Cr) in post-administration of PTH to the urinary excreted NAG (U/g Cr) in pre-administration of PTH for a value less than 2.3. The screening method provides the possibility of detecting renal lesions without clinical signs of diabetic nephropathy, using a preparation essentially consisting of active ingredient of PTH.

8 Claims, No Drawings

MONITORING METHOD OF RENAL LESIONS WITHOUT CLINICAL SIGNS

FIELD OF THE INVENTION

This invention relates to a novel screening method for renal lesions in diabetic patients not yet exhibiting symptoms of nephropathy, comprising administering a predetermined amount of parathyroid hormone, analogue thereof or derivative thereof (hereinafter sometimes simply designated as PTH) to patients with diabetes mellitus having an albumin excretion rate (AER) of less than 15 µg/min, measuring urinary excreted N-acetyl-β-D-glucosaminidase (NAG) and urinary creatinine in urinary samples taken 60±10 minutes prior to and after administration of PTH, and monitoring the ratio of urinary excreted NAG (U/g Cr) after administration of PTH to the urinary excreted NAG (U/g Cr) prior to administration of PTH for a value of less than 2.3.

More particularly, the present invention relates to method for early detection of diabetic nephropathy using a preparation essentially consisting of active ingredient of PTH.

BACKGROUND OF THE INVENTION

Disease of diabetes mellitus is primarily due to an insufficiency of insulin action. Clinical diagnosis of diabetes is defined generally by typical symptoms of diabetes mellitus showing thirsty, polyuria and weight loss, with hyperglycemia and overflow glycosuria, indicating a plasma glucose level of over 200 mg/dl, or if the above symptoms are found by a blood sugar determination with generally a glucose tolerance test. Diabetes mellitus is often accompanied with various complication and a prognosis of diabetes mellitus is influenced by the complications. Angiopathy, a major complication of diabetes mellitus, is mainly classified in the micro angiopathy including diabetic retinopathy and diabetic nephropathy, and the macroangiopathy including ischemic heart disease and cerebrovascular disorder.

Diabetic nephropathy is an important chronic complication for the prognosis of diabetes mellitus. Accordingly, an early detection of diabetic nephropathyand an early prevention of its progress would be extremely desirable. Symptoms of diabetic nephropathy are defined, as illustrated in the reference [Diabetic Nephropathy, Ed. Friedman, E. A., p.75 (1986), FIGS. 5–8], by observing the level of urinary protein in the patients, as a term of temporary increase in exercise-induced microalbumin excretion followed by detecting persistent proteinuria with a yearly increase in protein and a gradual decrease in creatinine clearance as a result of progressing nephropathy.

Heretofore diabetic nephropathy in patients having diabetes mellitus has been diagnosed by appearance of clinically detectable proteinurea. In this clinical stage, histopathological changes markedly progressed with decreased renal function and the lesions appeared to be irreversible [Diabetes, Vol. 32, Suppl. 2, p.64 (183) and Diabetic Nephropathy, Ed, Friedman, E. A., p.65 (1986)].

Recently, trace urinaryalbumin could be detected by radioimmunoassay, and nephropathycan be diagnosed at an early stage prior to detecting persistent proteinurea [Diabetes, Vol. 32, Suppl. 2, p. 64 (1983)]. In the event that urinary trace albumin is detected, then further continued progress of 6–14 years persistent proteinuria can be observed. Urinary trace albumin is generally expressed by AER from timed excretion of urine, and has a threshold value of 15–30 µg/min. The overflow value is defined as microalbuminuria and is diagnosed as diabetic nephropathy [Acta Endocrinol., 100:550 (1982), New Eng. J. Med., 331:89 (1983) and Lancet, 26:1430 (1982)].

Conventionally used parameters for reflecting renal function are urinary β2-microglubulin and urinary NAG [J. Clin. Invest., 48:1189 (1969) and Toxicology, 23:99 (1982)]. However, these parameters are not sensitive markers for early diagnosis of diabetic nephropathy.

In patients of early diabetic nephropathy with detected microalbuminuria, there is a known mechanism for affecting a glomerular filtration barrier. Transglomerular passage of plasma proteins depends on the following factors, including 1) structural changes of glomerular membrane, 2) changes in renal hemodynamics such as renal plasma flow and transcapillary hydraulic pressure and 3) filtration surface area abnormalities in pore-size or pore-charge level [Diabetes Care, 9(5):529 (1986)]. At present, however, there is no known method for finding out renal function of disease in the stage of diabetic renal lesion without clinical sign of nephropathy before detecting urinary trace albumin. Accordingly it is earnestly desired to detect patients with high risk of developing diabetic nephropathy for early diagnosis.

Natural human parathyroid hormone (PTH) is a polypeptide consisting of 84 amino acids secreted by parathyroid gland and its major physiological actions are stimulating bone resorption and bone formation in the bone, and suppressing reabsorption of phosphorus and stimulating reabsorption of calcium in renal tubules. Biological activities of PTH are involved at the N-terminal in its structure and chains 1–34 have almost the same biological activity as the whole molecule of PTH. Receptor of PTH exists mostly in renal proximal tubules.

Mizunashi et al. reported that intravenous administration of human PTH(1–34) [generic name: Teriparatide acetate, Trade name: human PTH inj. (ASAHI KASEI), Manufacturer: ASAHI CHEMICAL INDUSTRY CO. LTD.] in patients of idiopathic hypoparathyroidism (IHP) and pseudohypoparathyroidism (PHP) resulted in an increased urinary excretion of NAG in only IHP [Calcif. Tissue Int., 45(6):375 (1989)]. In addition, we have found that administration of human-PTH (1–34) in healthy volunteers resulted in an increased urinary excretion of NAG. Urinary NAG is a lysosomal enzyme widely located in renal proximal tubules, and is leaked from renal proximal tubular lysosome in the proximal tubular lesion, and is generally defined as a marker for toxicity of pharmaceuticals for the proximal tubular cells [Histochemistry, 63:245 (1979)].

SUMMARY OF THE INVENTION

The present invention provides novel laboratory detection method for diagnosing a renal function of the renal lesions without clinical signs of nephropathy prior to detecting any trace of urinary albumin, by observing increased urinary excretion of NAG by administering PTH to patients of diabetes mellitus having an AER of less than 15 µg/min. and being diagnosed with a range of normal renal function by the AER value. Routine laboratory testing method for early detection of decreased renal function is earnestly desired, accordingly the present invention also can be used as a laboratory test method therefor.

Further the present invention provides a new screening method for early diabetic nephropathy by applying a preparation of PTH as an active ingredient.

We have administered PTH intravenously into patients with diabetes mellitus, who were not diagnosed as diabetics of nephropathy, having an AER of urinary trace albumin of less than 15 µg/min., and measured urinary excretion of NAG and urinary creatinine in a collected urine within a period of 60±10 minutes before administration and in a collected urine within a period of 60±10 minutes after administration, then calculated the ratio of increased urinary excretion of NAG (U/g Cr) of post-administration to that of pre-administration, and found that there is a symptom showing a lower value of increased urinary NAG ratio of less than 2.3, which value out of the normal range (2.4–4.7) calculated by the response in healthy subjects. Accordingly we have found that, before deciding a diagnosis of nephropathy for patients with diabetes mellitus, there are some cases of symptom showing low reactivity of urinary excreted NAG for PTH as compared with reactivity of the subjects with normal renal function.

These facts indicated that the findings reflect the developing of some disorder in renal function. Accordingly, we have found that these findings can be used for a diagnosis of the renal lesions without clinical signs of nephropathy.

Applying the increased reaction of urinary NAG by administration of PTH for diagnosis of nephropathy, an abnormal stage of renal function prior to finding out detectable microalbuminuria and a diagnostic nephropathy, for which no diagnostic methods were known, can be detected at an earlier stage. Since a kidney disease, especially diabetic nephropathy is a disease which clinically requires early detection and early treatment, the above-reaction is found to be a useful diagnostic monitoring method for diabetic nephropathy.

The present invention has been completed by the above findings, and relates to a novel screening method for detecting renal lesions in diabetic patients not yet exhibiting symptoms of nephropathy comprising administering a predetermined dose of PTH to the patients with diabetes mellitus having an AER value of less than 15 μg/min., measuring urinary excreted NAG and urinary creatinine in urine samples take 60±10 minutes before and after administration of PTH, and checking the ratio of urinary excreted NAG (U/g Cr) prior to administration of PTH for a value of less than 2.3.

A renal lesion without clinical signs of nephropathy for the screening method in the present invention is defined as a condition for kidneys of patients with diabetes mellitus showing AER value being below 15 μg/min., and starting the crisis of latent abnormal renal function without detecting manifestable abnormal renal function.

Examples of formulations of PTH in the present invention are injections, rectal administering agents, percutaneous administrating agents and oral administrating agents, and these administration forms are not limitative. Preferable examples of injection are preparations for intravenous administration or subcutaneous administration. Examples of rectal administrating agents are generally rectal suppositories. Examples of percutaneous administrating agents are preparation for nasal administration and other transdermal absorbing agents. Examples of oral administrating agents are liposomes, microcapsules, and others.

PTH used in the present invention peptides of molecular weight of 4,000–10,000 or salt thereof having serum calcium increasing activity. Examples of peptides are peptides having 34–84 amino acids, and natural PTH or its analogues are known. For example, human PTH (abbrev. h-PTH) (1–84) [Biochem., 17:5723 (1973)], h-PTH(1–38) [Japan. Pat. Unexam. Publ. No. 57-81448), h-PTH (1–34) $NH_2$ (Japan. Pat. Unexam. Publ. No. 58-96052), [$Nle^{8,18}$] h-PTH (1–34), [$Nle^{8,18}$, $Tyr^{34}$] h-PTH(1–34) (IBID. No. 55-113753), [$Nle^{8,18}$] h-PTH(1–34)$NH_2$ (ibid. No. 61-24598), [$Nle^{8,18}$, $Tyr^{34}$] h-PTH(1–34)$NH_2$ (ibid. No. 60-24996), rat-PTH(1–84) [J. Biol. Chem., 259 (9):3320 (1984)], rat-PTH(1–34) [Endocrinal., 117 (3):1230 (1985)], bovine-PTH(1–84) [Am. J. Med., 50:639 (1971)], bovine-PTH (1–34) and bovine-PTH (1–34)$NH_2$[Pathobiology Annual, 11:53 (1981)] can be mentioned. Among them, a preferred example of PTH is h-PTH(1–34) having molecular weight about 4,400 with 34 imino acids sequence. Examples of salt thereof are pharmacologically acceptable non-toxic salt. Examples thereof are inorganic salt such as chloride or sulfate, and organic salt such as acetate, tartrate, succinate or malate. A preferred example is h-PTH (1–34) acetate (Teriparatide acetate).

The amount of administered PTH for monitoring is, for example in case of teriparatide acetate, preferably 10–400 teriparatide acetate units, more preferably 25–100 teriparatide acetate units and most preferably 50 teriparatide acetate units.

Biological activity of teriparatide acetate unit can be determined by a parallel test wherein reacting a membrane component of rat renal cortex with teriparatide acetate and assaying generated cAMP by radioimmunoassay. The specific activity of teriparatide acetate is 3,300 units/mg by a parallel test using the standard substance of bovine-PTH (1–84).

The predetermined dose of h-PTH(1–34), for example, is administered intravenously in the patients to carry out the monitoring method of the present invention. The patients are diabetes mellitus patients with an AER value below 15 μg/min., showing latent abnormal renal function without detecting manifestation of abnormal renal function. The h-PTH (1–34) is, for example, administered to these patients. Urinary excreted NAG of the patients can be assayed by hydrolysing a substrate NAG, i.e. sodium-cresol-sulfophthaleinyl-N-acetyl-β-D-glucosaminide (MCP-NAG), by NAG, coloring the thus generated m-cresol purple under alkaline condition by adding sodium carbonate and measuring colorimetrically 580 nm. Urinary NAG value is expressed, for example, as U/l (NAG active unit in one liter of urine). Urinary excreted NAG of the patients before administration of PTH and that after administration of PTH are measured, and an increased ratio of urinary excreted NAG value in the post-administration of PTH against the urinary excreted NAG value in the pre-administration of PTH is calculated.

Urine of the pre-administration is collected by excretion after accumulating the urine at a constant time interval, preferably 60 min.±10 min., previously after excreting urine in the pre-administration of PTH. Collecting urine is preferably performed immediately before administration of PTH. Urine of the post-administration is collected after accumulating the urine under the same condition in the pre-administration, i.e. after a constant time interval of 60 min.±10 min., because of performing excretion (collection) of urine immediately before administration of PTH. For effective accumulation of urine, a suitable amount of drinking water, for example 100–300 ml, may be given to the patients. Urinary NAG value can be measured using a specimen of 0.05–1 ml. Since a suitable volume of water is given to the patients, a correction of the NAG value is needed. Accordingly, a parameter of urine volume and concentration, for example another component such as urinary creatinine concentration (expressed as mg/dl) is measured, and NAG value per creatinine value is obtained. A corrected value of NAG for creatinine (Unit: U/g Cr) is calculated by;

Urinary NAG (U/l)÷urinary creatinine (mg/dl)×100.

In the increased ratio of NAG value obtained hereinabove, if the time interval of collecting urine before and after administration of PTH is set to 60 min.±10 min., and the resultant increased ratio is over 2.4, the monitoring result can be diagnosed as healthy kidneys, and if the ratio is below 2.3 the kidney is diagnosed as having renal lesions without clinical signs of nephropathy with latent abnormal renal function but without manifestation of abnormal renal function. Therefore early diabetic nephropathy can be monitored in the patients.

In the present invention, the ratio of increase in the urinary excretion of NAG after administration of PTH to the urinary excretion of NAG before administration of PTH is calculated on the basis of a time interval from collection of urine before the administration to that of after the administration being set at 60 min.±10 min., however the time interval time need not necessarily to be limited to 60 min.±10 min. The time interval may be set by taking into account the increased ratio of NAG value calculated based on the standard value range in healthy subjects.

According to the present invention, the diabetes mellitus patients having renal lesions not yet exhibiting symptoms of nephropathy with latent abnormal renal function but without manifestation of abnormal renal function can be diagnosed in their crisis of diabetic nephropathy in early stage by monitoring the early stage of diabetic nephropathy, and its progress can be prevented by, for example, diet therapy and nursing system. The method of the present invention has an advantage as compared with conventional diagnostic method of measuring trace urinary albumin, a parameter for diagnosing early diabetic nephropathy.

EFFECT OF THE INVENTION

The present invention provides the possibility of detecting abnormal reaction of renal function before detecting any trace of urinary albumin by conventional methods, and a more sensitive monitoring method of renal function as compared with the conventional known methods. Accordingly, the present diagnostic method is useful for preventing crisis and progress of renal failure, especially diabetic nephropathy.

EXAMPLES

The following examples illustrate the present invention, but are not to be construed as limiting.

EXAMPLE 1

Parathyroid hormone 7.2 mg (Teriparatide hydrochloride, 3,333 teriparatide acetate units/mg) and filler were dissolved in distilled water for injection 100 ml, passed through filter for sterilization, filled each 0.5 ml in a vial and lyophilized. Vials were filled with nitrogen gas as tightly sealed by a rubber stopper to obtain the preparation for injection. The preparation for injection thus prepared is dissolved before used as in the examples hereinbelow.

REFERENTIAL EXAMPLE

Method: Fourteen (14) healthy male volunteers were used.

Prior to 60 minutes for intravenous administration of h-PTH(1–34) 100 units, complete excretion of urine was performed. 200 ml of drinking water was given to the individual volunteers and urine was collected immediately before administration of h-PTH(1–134). Then, h-PTH(1–34) 100 units were administered intravenously and 200 ml of drinking water was given to the volunteers, and after 60 minutes urine was again collected. Each of urinary NAG and creatinine in 0.5 ml of urine was measured, and an increased ratio of urinary excreted NAG was calculated. NAG value was corrected by creatinine value.

For an assay of NAG, NAG Test Shionogi (Shionogi Pharm. Co., assay method: mcp colorimetry) was used, and for that of creatinine, creatinine-HR (Wako Pure, Chem. Co., assay method: alkali picric acid method) was used. The result is shown in Table 1. Table 1 illustrates the various parameters, i.e. NAG, AER and serum Cr, in pre- or post-administration of PTH for healthy male volunteers.

TABLE 1

| Name of volunteers | Age (year) | Urinary NAG pre- (U/gCr) | Urinary NAG post- (U/gCr) | Urinary NAG changes (U/gcr) | Urinary NAG changes in ratio (ratio) | AER (urine) (µg/min) | Serum Cr (mg/dl) |
|---|---|---|---|---|---|---|---|
| S.S | 46 | 1.6 | 5.9 | 4.3 | 3.8 | 2.9 | 1.0 |
| E.O | 28 | 2.2 | 8.6 | 6.4 | 3.9 | 3.3 | 1.2 |
| T.M | 35 | 3.2 | 10.7 | 7.4 | 3.3 | 3.6 | 0.9 |
| Si.Ta | 36 | 1.3 | 5.7 | 4.4 | 4.4 | 3.9 | 1.0 |
| Fu.Si | 21 | 2.4 | 7.3 | 4.9 | 3.1 | 4.3 | 1.1 |
| H.F | 46 | 3.0 | 11.0 | 8.1 | 3.7 | 4.3 | 1.0 |
| M.O | 52 | 5.1 | 14.7 | 9.7 | 2.9 | 4.5 | 0.9 |
| Y.I | 50 | 5.5 | 17.0 | 11.5 | 3.1 | 4.6 | 0.9 |
| Hi.Iw | 42 | 2.8 | 10.0 | 7.3 | 3.6 | 5.1 | 0.8 |
| Sa.Ta | 47 | 4.4 | 19.3 | 15.0 | 4.4 | 7.1 | 0.9 |
| T.K | 21 | 1.5 | 6.4 | 4.9 | 4.1 | 7.3 | 1.1 |
| M.H | 27 | 2.5 | 8.3 | 5.8 | 3.4 | 7.5 | 1.0 |
| Fu.Sa | 30 | 3.5 | 9.8 | 6.3 | 2.8 | 7.6 | 0.9 |
| K.H | 49 | 3.8 | 10.0 | 6.2 | 2.6 | 8.1 | 0.9 |
| No. of cases | 14 | 14 | 14 | 14 | 14 | 14 | 14 |
| Mean | 38 | 3.0 | 10.3 | 7.3 | 3.5 | 5.3 | 1.0 |
| S.D. | 11 | 1.3 | 4.1 | 3.0 | 0.6 | 1.8 | 0.1 |

Result: Expressing the measured result by mean ± S.D., each value of NAG in pre- and post-administration is 3.0±1.3 U/g Cr, and 10.3±4.1 U/g Cr, respectively. The increased ratio of urine excreted NAG in post-administration to pre-administration is 3.5±0.6. (Table 1)

NAG value corrected by creatinine (unit: U/g Cr) is calculated by the equation;

Urinary NAG (Unit:U/l)÷urinary creatinine (unit:mg/dl)×100.

The normal range of urinary NAG value after administration of PTH in healthy volunteers is defined according to the results obtained hereinabove as follows. The normal range is calculated by mean ±2 S.D.

NAG value before administration: 0.4–5.6 U/g Cr.

NAG value after administration: 2.2–18.5 U/g Cr, and the increased ratio of urinary NAG in post-administration to pre-administration: 2.4–4.7

EXAMPLE 2

Method: Eighteen (18) patients with diabetes mellitus having AER within normal range (below 15 µg/min.) were used.

Sixty minutes prior to intravenous administration of 100 units of h-PTH(1–34), complete excretion of urine was performed. 200 ml of drinking water were given to the individual volunteers and urine was collected immediately before administration of h-PTH(1–34). Then 100 units of h-PTH(1–34) were administered intravenously and 200 ml of drinking water were given for intake, and after 60 minutes urine was collected. Each of urinary NAG and creatinine in 0.5 ml of urine was measured to calculate the increased ratio of urinary excreted NAG. The NAG value was corrected by creatinine value.

The results are shown in Tables 2 and 3. Tables 2 and 3 show the various parameters in pre- and post-administration of PTH for the patients of diabetes mellitus showing the value with the normal range of AER (below 15 µg/min.).

Result: In the patients having diabetes mellitus, an increased ratio of urinary excreted NAG value in 6 subjects showed normal value (2.4–4.7) and significantly decreased values were observed in 12 cases (2.3) and were diagnosed as renal lesion without clinical symptoms of nephropathy (Tables 2 and 3). The normal range is calculated by mean ±2 S.D. in the same manner as in the referential example hereinabove.

TABLE 2

| Name of patients | Age (year) | Urinary NAG pre- (U/gCr) | AER (Urine) (µg/min) | Serum Cr (mg/dl) | Serum HbAlc (%) | FBS* (mg/dl) | Term of disease (month) | Diagonosis of renal function |
|---|---|---|---|---|---|---|---|---|
| Y.S | 51 | 3.9 | 1.6 | 0.9 | 13.3 | 121 | — | renal lesions without clinical sign |
| Hi.Ka | 56 | 3.9 | 1.7 | 1.0 | 10.1 | 130 | 70 | " |
| T.Ki | 52 | 7.7 | 2.6 | 0.8 | 8.4 | 153 | 34 | " |
| R.H | 51 | 3.8 | 2.8 | 0.8 | 9.7 | 122 | 60 | " |
| Ko.M | 31 | 3.9 | 3.0 | 1.7 | 12.6 | 92 | 48 | normal kidney |
| H.To | 35 | 7.2 | 3.7 | 0.9 | 11.9 | 121 | 2 | renal lesions without clinical sign |
| Hi.Ko | 37 | 3.1 | 5.0 | 1.1 | 5.8 | 117 | 48 | " |
| F.T | 58 | 10.0 | 5.0 | 1.0 | 5.5 | 131 | 4 | " |
| I.T | 52 | 4.3 | 5.4 | 0.7 | 7.3 | 118 | 142 | normal kidney |
| M.D | 50 | 3.6 | 6.9 | 0.8 | 10.8 | 106 | 1 | " |
| T.I | 44 | 6.3 | 9.4 | 0.9 | 10.5 | 199 | 103 | renal lesions without clinical sign |
| Mas.S | 60 | 2.3 | 10.1 | 1.1 | 4.8 | 98 | 36 | " |
| M.Ad | 47 | 11.2 | 11.0 | 0.9 | 9.1 | 149 | 76 | " |
| S.O | 58 | 5.3 | 13.0 | 1.0 | 12.6 | 277 | 34 | normal kidney |
| H.Te | 66 | 6.5 | 13.7 | 1.1 | 7.7 | 147 | 139 | " |
| S.F | 41 | 4.6 | 13.8 | 0.8 | 11.8 | 161 | 36 | renal lesions without clinical sign |
| T.Ko | 61 | 2.9 | 14.3 | 1.0 | 8.8 | 144 | 82 | " |
| Yu.M | 62 | 5.0 | 14.3 | 1.2 | 5.4 | 89 | 68 | normal kidney |
| No. of cases | 18 | 18 | 18 | 18 | 19 | 18 | 17 | |
| Mean | 51 | 5.3 | 7.6 | 1.0 | 9.2 | 138 | 58 | |
| S.D. | 10 | 2.4 | 4.8 | 0.2 | 2.7 | 44 | 44 | |

*Fasting blood sugar level

TABLE 3

| Name of patients | Age (year) | Urinary NAG pre- (U/gCr) | Urinary NAG post- (U/gCr) | Urinary NAG changes (U/gcr) | Urinary NAG changes in ratio (ratio) | AER (urine) (µg/min) | Diagonosis of renal function |
|---|---|---|---|---|---|---|---|
| Y.S | 51 | 3.9 | 7.3 | 3.4 | 1.9 | 1.6 | renal lesions without clinical sign |
| Hi.Ka | 56 | 3.9 | 7.8 | 3.9 | 2.0 | 1.7 | " |
| T.Ki | 52 | 7.7 | 15.6 | 7.9 | 2.0 | 2.6 | " |
| R.H | 51 | 3.8 | 7.5 | 3.7 | 2.0 | 2.8 | " |
| Ko.M | 31 | 3.9 | 11.0 | 7.1 | 2.8 | 3.0 | normal kidney |
| H.To | 35 | 7.2 | 12.2 | 4.9 | 1.7 | 3.7 | renal lesions without clinical sign |
| Hi.Ko | 37 | 3.1 | 6.8 | 3.7 | 2.2 | 5.0 | " |
| F.T | 58 | 10.0 | 17.5 | 7.5 | 1.8 | 5.0 | " |
| I.T | 52 | 4.3 | 10.1 | 5.8 | 2.4 | 5.4 | normal kidney |
| M.D | 50 | 3.6 | 15.3 | 11.7 | 4.3 | 6.9 | " |
| T.I | 44 | 6.3 | 10.1 | 3.9 | 1.6 | 9.4 | renal lesions without clinical sign |
| Mas.S | 60 | 2.3 | 4.5 | 2.2 | 2.0 | 10.1 | " |
| M.Ad | 47 | 11.2 | 23.9 | 12.7 | 2.1 | 11.0 | " |
| S.O | 58 | 5.3 | 13.4 | 8.1 | 2.5 | 13.0 | normal kidney |
| H.Te | 66 | 6.5 | 15.9 | 9.3 | 2.4 | 13.7 | " |
| S.F | 41 | 4.6 | 9.7 | 5.1 | 2.1 | 13.8 | renal lesions without clinical sign |
| T.Ko | 61 | 2.9 | 6.7 | 3.7 | 2.3 | 14.3 | " |

TABLE 3-continued

| Name of patients | Age (year) | Urinary NAG pre- (U/gCr) | Urinary NAG post- (U/gCr) | Urinary NAG changes (U/gcr) | Urinary NAG changes in ratio (ratio) | AER (urine) (μg/min) | Diagonosis of renal function |
|---|---|---|---|---|---|---|---|
| Yu.M | 62 | 5.0 | 16.7 | 11.7 | 3.4 | 14.3 | normal kidney |
| No. of cases | 18 | 18 | 18 | 18 | 18 | 18 | |
| Mean | 51 | 5.3 | 11.8 | 6.5 | 2.3 | 7.6 | |
| S.D | 10 | 2.4 | 5.0 | 3.2 | 0.7 | 4.8 | |

The normal range of AER is cited from Mogensen et al., New England J. Med., 331:89 (1984).

As shown above, the patients who were diagnosed within the normal range of AER measured by the most sensitive conventional measuring method calculated by a parameter of trace albumin at present, were clearly demonstrated as having renal lesions without clinical signs of nephropathy by measuring NAG increased ratio for an action of PTH.

We claim:

1. A screening method for renal lesions in diabetic patients not yet exhibiting symptoms of nephropathy, comprising administering a predetermined dose of a parathyroid hormone, analogue or derivative thereof to the patients, and measuring urinary excreted N-acetyl-β-D-glucosaminidase (NAG).

2. The screening method according to claim 1, wherein the parathyroid hormone is h-PTH (1–34) acetate (teriparatide acetate).

3. The screening method according to claim 2, wherein the teriparatide acetate contains 10–400 teriparatide acetate units.

4. The screening method according to claim 1 wherein the parathyroid hormone is administered intravenously.

5. A screening method for renal lesions in diabetic patients not yet exhibiting symptoms of nephropathy, comprising administering a predetermined dose of parathyroid hormone, analogue or derivative thereof (PTH) to the patients having an albumin excretion rate (AER) less than 15 μg/min., measuring urinary excreted N-acetyl-β-D-glucosaminidase (NAG) and urinary creatinine in urine samples taken 60±10 minutes before and after administration of PTH and monitoring a ratio of urinary excreted NAG-creatinine after administration of PTH to the urinary excreted NAG-creatinine before administration of PTH for a value of less than 2.3.

6. The screening method according to claim 5, wherein a normal range of ratio of the urinary excreted NAG value after administration of PTH to the urinary excreted NAG value before administration of PTH in healthy subjects is 2.4 to 4.7.

7. A method for early detection of renal lesions in diabetic patients not yet exhibiting symptoms of nephropathy, comprising administering a predetermined dose of parathyroid hormone, an analogue or a derivative thereof to said patients, measuring urinary excreted N-acetyl-β-D-glucosaminidase (NAG) after said administration, and comparing an amount of urinary excreted NAG after said administration to an amount of urinary excreted NAG prior to said administration.

8. The method according to claim 7, wherein said patients have an albumin excretion rate (AER) of microalbumin below 15 μh/min.

* * * * *